(12) United States Patent
Mita et al.

(10) Patent No.: US 6,534,499 B2
(45) Date of Patent: Mar. 18, 2003

(54) N-SUBSTITUTED-N'-SUBSTITUTED UREA DERIVATIVES AND THE USE THEREOF AS TNF-α PRODUCTION INHIBITORY AGENTS

(75) Inventors: Shiro Mita, Osaka (JP); Masato Horiuchi, Osaka (JP); Masakazu Ban, Osaka (JP); Hiroshi Suhara, Osaka (JP)

(73) Assignee: Santen Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 09/969,589

(22) Filed: Oct. 4, 2001

(65) Prior Publication Data

US 2002/0077357 A1 Jun. 20, 2002

Related U.S. Application Data

(63) Continuation of application No. PCT/JP00/02267, filed on Apr. 7, 2000.

(30) Foreign Application Priority Data

Apr. 7, 1999 (JP) .............................. 11-100482

(51) Int. Cl.⁷ ................... C07D 207/09; C07D 207/20; C07D 295/14; A61K 31/40; A61K 31/4453
(52) U.S. Cl. ............... 514/217.12; 514/237.8; 514/252.12; 514/331; 514/428; 540/609; 540/610; 544/168; 544/400; 546/231; 546/233; 546/332; 546/336; 546/337; 548/565; 548/567
(58) Field of Search ................ 540/609, 610; 544/168, 400; 546/231, 233, 332, 336, 337; 548/565, 567; 514/217.12, 237.8, 252.12, 331, 428

(56) References Cited

U.S. PATENT DOCUMENTS 5,190,974 A   3/1993   Clemence et al. .......... 514/513

2001/0041725 A1 * 11/2001 Mita et al. ................. 514/357

FOREIGN PATENT DOCUMENTS

WO        00/07985        2/2000

OTHER PUBLICATIONS

Yamazaki, M., "Processing and regulation of tumor necrosis factor–α,", *Clinical Immunology*, 1995, vol. 27, No. 10, pp. 1270–1274, Academic Press, San Diego, California.

Eigler, A. et al., "Taming TNF: strategies to restrain this proinflammatory cytokine", *Immunology Today*, 1997, vol. 18, No. 10, pp. 487–492, Elsevier, New York, New York.

* cited by examiner

*Primary Examiner*—Deepak Rao
(74) *Attorney, Agent, or Firm*—Burns, Doane, Swecker & Mathis, LLP

(57) ABSTRACT

N-Substituted-N'-substituted urea derivatives represented by the following formula, analogs thereof or pharmaceutically acceptable salts thereof are herein provided. These compounds show a TNF-α production inhibitory activity.

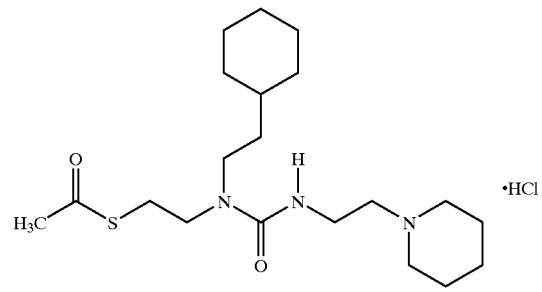

19 Claims, No Drawings

N-SUBSTITUTED-N'-SUBSTITUTED UREA DERIVATIVES AND THE USE THEREOF AS TNF-α PRODUCTION INHIBITORY AGENTS

This application is a continuation of International Application No. PCT/JP00/002267 filed on Apr. 7, 2000, which International Application was published by the International Bureau in Japanese on Oct. 19, 2000.

BACKGROUND OF THE INVENTION

The present invention relates to a novel N-substituted-N'-substituted urea derivative, a pharmaceutical composition containing the same, a TNF-α production inhibitory agent and a therapeutic agent for treating an autoimmune disease.

TNF-α (Tumor Necrosis Factor-α) has presently been recognized as a cytokine strongly correlated with biological protection-immunological mechanism, but the continuous and excess production of TNF-α causes various tissue disorders and this accordingly becomes a principal cause of a variety of diseases and exacerbation. For instance, examples of pathogenesis associated with TNF-α include articular rheumatism, systemic erythematodes (SLE), dyscrasia, acute infectious diseases, allergy, fever, anemia and diabetes (YAMAZAKI, Clinical Immunology, 1995, 27:1270). Moreover, it has also been reported that TNF-α plays an important role in the crisis of chronic rheumatism and Crohn's disease, which are autoimmune diseases (Andreas Eigler et al., Immunology Today, 1997, 18:487).

Accordingly, a compound capable of inhibiting the production of TNF-α or controlling the action thereof would be effective in the treatment of the foregoing diseases and therefore, a variety of investigations have been done to obtain such a compound (the foregoing articles: YAMAZAKI, Clinical Immunology, 27; Andreas Eigler et al., Immunology Today, 18).

DISCLOSURE OF THE INVENTION

An object of the present invention is to provide a novel compound having an activity of inhibiting TNF-α production.

It is another object of the present invention to provide an intermediate useful in the preparation of the foregoing compound.

It is a further object of the present invention to provide a pharmaceutical composition containing the foregoing compound, a TNF-α production inhibitory agent and a therapeutic agent for treating autoimmune diseases.

The inventors of this invention have conducted intensive studies to synthesize a compound having a urea structure as a basic structure, which has not conventionally been investigated as a drug, have established a large number of novel compounds, have found that N-substituted-N'-substituted urea derivatives represented by the following general formula I among the foregoing novel compounds show an excellent TNF-α production inhibitory activity and thus have completed the present invention on the basis of the foregoing finding.

More specifically, the present invention herein provides an N-substituted-N'-substituted urea derivative represented by the following general formula I as well as a pharmaceutically acceptable salt thereof:

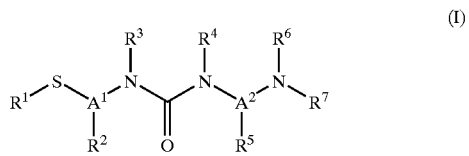

wherein $R^1$ represents a hydrogen atom, a lower alkyl group, an aryl group or a group represented by the following general formula II:

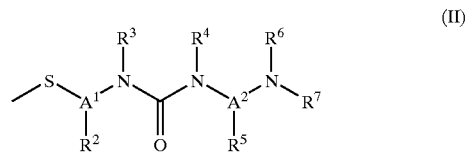

wherein $R^2$ represents a hydrogen atom, a lower alkyl group, a cycloalkyl group, an aryl group, a carboxyl group or an ester group, or $R^2$ may form a ring together with $R^1$; $R^3$ and $R^4$ may be the same or different and each represents a hydrogen atom, a lower alkyl group, a cycloalkylalkyl group, an adamantylalkyl group, an arylalkyl group, a cycloalkyl group or an aryl group; $R^5$ represents a hydrogen atom, a lower alkyl group, a hydroxyl group, a lower alkoxy group or an aryl group; $R^6$ and $R^7$ may be the same or different and each represents a hydrogen atom, a lower alkyl group, a cycloalkylalkyl group, a cycloalkyl group or an aryl group; $A^1$ and $A^2$ may be the same or different and each represents a lower alkylene group, provided that $R^5$ and either $R^6$ or $R^7$ together or $R^6$ and $R^7$ together form a 5- to 7-membered ring and that either of the substituents $R^3$ and $R^4$ represents a cycloalkylalkyl group, an adamantylalkyl group or an arylalkyl group.

According to the present invention, there are also provided N-substituted-N'-substituted urea derivatives represented by the following general formula III as well as salts thereof:

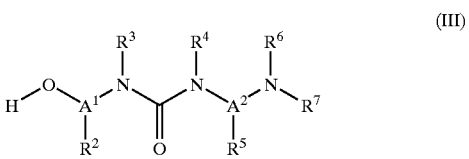

The present invention likewise provides a pharmaceutical composition, a TNF-α production inhibitory agent and a therapeutic agent for treating autoimmune diseases, which comprise the foregoing N-substituted-N'-substituted urea derivative or a pharmaceutically acceptable salt thereof.

BEST MODE FOR CARRYING OUT THE INVENTION

In the present invention, the lower alkyl group may be, for instance, linear or branched alkyl groups having 1 to 8 carbon atoms such as methyl, ethyl, propyl, isopropyl, butyl, isobutyl, t-butyl, pentyl, isopentyl and isohexyl groups, with alkyl groups having 1 to 6 being preferred. The lower alkyl group is more preferably those having 1 to 3 carbon atoms, in particular, methyl group. Examples of cycloalkyl groups are those having 3 to 10 carbon atoms such as cyclopropyl, cyclobutyl, cyclopentyl, cyclohexyl and cycloheptyl groups, with those having 3 to 6 carbon atoms being preferred and cyclohexyl group being particularly preferred. Examples of lower alkoxy groups include linear or branched alkoxy groups having 1 to 8 carbon atoms such as methoxy, ethoxy, propoxy, isopropoxy, butoxy and hexyloxy groups, with those having 1 to 5 carbon atoms being preferred and those having 1 to 3 carbon atoms being particularly preferred.

These lower alkyl, cycloalkyl and lower alkoxy groups may be substituted wiTNFor instance, halogen atoms (such as fluorine, chlorine, iodine and bromine atoms) and/or a hydroxyl group. Moreover, the cycloalkyl group may be substituted with a lower alkyl group and/or a lower alkoxy group.

Examples of lower alkylene groups are linear or branched alkylene groups having 1 to 8 carbon atoms such as methylene, ethylene, propylene, isopropylene, methylmethylene, tetramethylene, 2-methyltrimethylene and hexamethylene groups, with those having 1 to 5 carbon atoms being preferred. The lower alkylene group is more preferably those having 2 to 4 carbon atoms and in particular, those having 2 to 3 carbon atoms.

In addition, examples of aryl groups are phenyl groups, naphthyl groups and aromatic heterocyclic groups having 6 to 12 carbon atoms, which may be substituted or unsubstituted and the aryl group is preferably a substituted or unsubstituted phenyl group and particularly preferably an unsubstituted phenyl group or a biphenylyl group. In this respect, the substituent may be, for instance, a halogen atom (such as fluorine, chlorine, iodine or bromine atom), a hydroxyl group, an amino group, a lower alkyl group, a lower alkoxy group, a cycloalkyl group or a phenyl group.

Examples of cycloalkylalkyl, adamantylalkyl and arylalkyl groups are linear or branched alkyl groups having 1 to 8 carbon atoms, preferably alkyl groups having 1 to 5 carbon atoms, more preferably alkyl groups having 1 to 3 carbon atoms and most preferably ethyl group, to which the foregoing cycloalkyl, adamantly or aryl group is bonded.

Examples of ester groups are lower alkyl esters, benzyl esters and phenyl esters.

Examples of rings formed by the combination of substituents $R^2$ and $R^1$ are 5- and 6-membered non-aromatic hetero rings including the sulfur atom to which $R^1$ is bonded as a member of the rings, such as tetrahydrothiophene, thiolactone and dithiolan.

Examples of 5- to 7-membered rings formed by the combination of $R^6$ with $R^6$ or $R^7$ or the combination of $R^6$ and $R^7$ are non-aromatic hetero rings having a nitrogen atom or a combination of a nitrogen atom and an oxygen or sulfur atom in the ring, with those having one or two nitrogen atoms and those having a nitrogen atom and an oxygen atom being more preferred. Specific examples thereof include pyrroline, pyrrolidine, oxazoline, oxazolidine, thiazoline, thiazolidine, imidazoline, imidazolidine, pyrazoline, pyrazolidine, dihydropyridine, tetrahydropyridine; piperidine, piperazine, morpholine, homo-piperazine and homo-piperidine rings. Among these rings, preferred are pyrroline, pyrrolidine, tetrahydropyridine, piperidine, piperazine, morpholine and homo-piperidine rings, with pyrrolidine, piperidine, piperazine, tetrahydropyridine and homo-piperidine rings being more preferred. Particularly preferably used herein are pyrrolidine, piperidine and homo-piperidine rings. These 5- to 7-membered rings may be substituted wiTNFor instance, lower alkyl groups, lower alkylamino groups, amino groups and/or hydroxyl group or may be condensed with a benzene ring.

When the compound represented by the general formula I according to the present invention has thiol, hydroxyl, amino and/or nitrogen atom-containing hetero ring, these groups may be protected with commonly used protective groups.

Examples of protective groups for thiol group are those commonly used as protective groups for thiol group such as acyl groups and substituted thio groups. Specific examples thereof are acyl groups such as lower alkanoyl groups, phenylcarbonyl groups, thenoyl groups, nicotinoyl groups, lower alkoxycarbonyl groups, substituted lower alkoxycarbonyl groups and substituted carbamoyl groups; and substituted thio groups such as lower alkylthio groups and phenylthio group. In this connection, the phenyl rings of the foregoing phenylcarbonyl and phenylthio groups may be substituted with a halogen atom, a lower alkyl group, a lower alkoxy group or a nitro group.

Among these, preferred are, for instance, acyl groups such as acetyl group, propionyl group, butyryl group, pivaloyl group, benzoyl group, thenoyl group, t-butoxycarbonyl group and benzyloxycarbonyl group; and substituted thio groups such as ethylthio, t-butylthio and phenylthio groups, with lower alkylcarbonyl groups (in particular, those having 2 to 5 carbon atoms) being more preferably used.

Protective groups for hydroxyl group may be, for instance, those commonly used as the protective groups for hydroxyl group such as acyl groups, substituted lower alkyl groups and substituted silyl groups. Specific examples thereof are acyl groups such as formyl group, lower alkanoyl groups, halogenated lower alkanoyl groups, phenylcarbonyl groups, lower alkoxycarbonyl groups and phenyl lower alkoxycarbonyl groups; substituted lower alkyl groups such as allyl group, lower alkoxy lower alkyl groups, substituted lower alkoxy lower alkyl groups, phenyl lower alkyl groups, tetrahydropyranyl groups and tetrahydrofuranyl groups; and substituted silyl groups such as lower alkyl silyl groups and phenyl silyl group. In this respect, the phenyl rings of the foregoing phenylcarbonyl, phenyl lower alkoxycarbonyl, phenyl lower alkyl and phenyl silyl groups may be substituted with a halogen atom, a lower alkyl group, a lower alkoxy group or a nitro group.

Among these, preferably used as such protective groups are acyl groups such as formyl, acetyl, pivaloyl, monochloroacetyl, trichloroacetyl, trifluoroacetyl, benzoyl, methoxycarbonyl, ethoxycarbonyl, isobutoxycarbonyl, t-butoxycarbonyl and benzyloxy- carbonyl groups; substituted alkyl groups such as allyl, methoxymethyl, 1-ethoxyethyl, 2-methoxyethoxymethyl, benzyloxymethyl, benzyl, 4-methoxybenzyl, trityl, 2-tetra- hydropyranyl and 2-tetrahydrofuranyl groups; and substituted silyl groups such as trimethyl silyl, triethyl silyl, triisopropyl silyl, t-butyldimethyl silyl and t-butyldiphenyl silyl groups, with tri(lower alkyl) silyl groups being more preferred.

Examples of protective groups for amino and nitrogen atom as a member of a hetero ring are those commonly used as protective groups for amino and nitrogen atom as a member of a hetero ring such as acyl groups, substituted lower alkyl groups and substituted sulfonyl groups. Specific examples thereof are acyl groups such as formyl, lower alkanoyl, halogenated lower alkanoyl, phenylcarbonyl, lower alkoxycarbonyl, substituted lower alkoxycarbonyl and phenoxycarbonyl groups; substituted lower alkyl groups such as allyl, phenyl lower alkyl and benzoyl lower alkyl groups; and substituted sulfonyl groups such as lower alkylsulfonyl and phenylsulfonyl groups. In this connection, the phenyl rings of the foregoing phenylcarbonyl, phenoxycarbonyl, phenyl lower alkyl, benzoyl lower alkyl and phenylsulfonyl groups may be substituted with a halogen atom, a lower alkyl group, a lower alkoxy group or a nitro group.

Among these protective groups, preferred are acyl groups such as formyl, acetyl, trichloroacetyl, trifluoroacetyl, benzoyl, methoxycarbonyl, isobutoxycarbonyl, t-butoxycarbonyl, allyloxycarbonyl, 2,2,2-trichloroethoxycarbonyl, benzyloxycarbonyl, diphenylmethoxycarbonyl and phenoxycarbonyl groups; substituted alkyl groups such as allyl, benzyl, trityl and (4-methoxyphenyl) diphenylmethyl; and substituted sulfonyl groups such as benzenesulfonyl, 2,4,6-trimethylbenzenesulfonyl and toluenesulfonyl groups, with lower alkoxycarbonyl groups being more preferred.

In the compound of Formula I according to the present invention, $R^1$ is preferably a hydrogen atom, a lower alkyl group or a group represented by Formula II and if $R^1$ represents a hydrogen atom, preferred compounds include those protected with thiol protective groups. Moreover, $R^1$ is preferably a hydrogen atom or a lower alkyl group and if $R^1$ represents a hydrogen atom, preferred compounds include those necessarily protected with thiol protective groups. In addition, if $R^1$ is a lower alkyl group, the lower alkyl group is preferably an unsubstituted one.

The substituent $R^2$ is preferably a hydrogen atom or an aryl group, with hydrogen atom being particularly preferred. If $R^2$ is an aryl group, the aryl group is preferably bonded to the $2^{nd}$ or $3^{rd}$ carbon atom of the substituent $A^1$, while the carbon atom of $A^1$ bonded to the S atom is defined to be the $1^{st}$ carbon atom, with the aryl group bonded to the $2^{nd}$ carbon atom of the substituent $A^1$ being more preferred.

$R^3$ and $R^4$ may be the same or different and each preferably represents a hydrogen atom, a lower alkyl group, a cycloalkylalkyl group, an adamantylalkyl or an arylalkyl group. $R^3$ is preferably a cycloalkylalkyl group, an adamantylalkyl group or an arylalkyl group, with a cycloalkylalkyl group and an adamantylalkyl group being particularly preferred. $R^4$ is preferably a hydrogen atom, a lower alkyl group or an arylalkyl group, with a hydrogen atom being particularly preferred.

In particular, the foregoing substituents $R^3$ and $R^4$ are different from one another. Among these, one of them preferably represents a hydrogen atom and $R^4$ preferably represents a hydrogen atom. The lower alkyl groups represented by the substituents $R^3$ and $R^4$ are preferably linear or branched alkyl groups having 4 to 8 carbon atoms.

The substituent $R^5$ preferably represents a hydrogen atom, a lower alkyl group, a hydroxyl group or an aryl group, with a hydrogen atom, a lower alkyl group and an aryl group being more preferred. If $R^5$ represents a hydroxyl group, it may be protected with a hydroxyl group-protecting group. If $R^5$ represents a group other than a hydrogen atom, $R^5$ is preferably bonded to the $1^{st}$, $2^{nd}$ or $3^{rd}$ carbon atom of the substituent $A^2$, while the carbon atom of the substituent $A^2$ bonded to the nitrogen atom constituting a urea is defined to be the $1^{st}$ carbon atom. More preferably, $R^5$ is bonded to the $1^{st}$ or $2^{nd}$ carbon atom of the substituent $A^2$.

$R^6$ and $R^7$ may be the same or different and each preferably represents a hydrogen atom, a lower alkyl group or an aryl group, with a lower alkyl group being more preferred. $A^1$ and $A^2$ may be the same or different and each preferably represents a lower alkylene group having 2 to 4 carbon atoms and, in particular, $A^1$ is preferably a lower alkylene group having 2 or 3 carbon atoms.

In the general formula I, the 5- to 7-membered ring formed by the combination of the substituents $R^5$ and $R^5$ (or $R^7$) may be those listed above, but particularly preferred are pyrrolidine and piperidine rings. Among the 5- to 7-membered ring formed from $R^6$ and $R^7$, preferred are those listed above.

Among the compounds of the present invention represented by Formula I, preferred are those listed below:

(i) Compounds of Formula I wherein $R^1$ is a hydrogen atom or a lower alkyl group, $R^2$ is a hydrogen atom or an aryl group, $R^3$ and $R^4$ may be the same or different and each represents a hydrogen atom, a lower alkyl group, a cycloalkylalkyl group, an adamantylalkyl group or an arylalkyl group, $R^5$ is a hydrogen atom, a lower alkyl group, a hydroxyl group or an aryl group, $R^6$ and $R^7$ may be the same or different and each represents a hydrogen atom, a lower alkyl group or an aryl group, and $A^1$ and $A^2$ may be the same or different and each represents an alkylene group having 2 or 3 carbon atoms.

(ii) Compounds of Formula I wherein $R^6$ and $R^7$ represents hydrogen atoms or lower alkyl groups, $A^1$ is an alkylene group having 2 carbon atoms and $A^2$ is an alkylene group having 2 or 3 carbon atoms, in addition to the foregoing definition (i).

(iii) Compounds of Formula I wherein $R^3$ is a cycloalkylalkyl group, an adamantylalkyl group or an arylalkyl group and $R^4$ is a hydrogen atom, in addition to the foregoing definition (i) or (ii).

(iv) Compounds of Formula I wherein $R^5$ is a hydrogen atom; a lower alkyl group or an aryl group, $R^6$ and $R^7$ form a 5- to 7-membered ring together, in addition to the foregoing definition (i) to (iii).

(v) In the foregoing definition (iv), the 5- to 7-membered ring formed from $R^6$ and $R^7$ may further comprise a nitrogen, oxygen or sulfur atom, or may comprise a double bond.

(vi) In the foregoing definition (i) to (iii), $R^5$ and $R^6$ or $R^7$ form a 5- to 7-membered ring and $R^6$ or $R^7$, which is not involved in the formation of a ring, is a lower alkyl group.

(vii) In the foregoing definition (i) to (vi), if $R^1$ is a hydrogen atom, it is protected with a lower alkylcarbonyl group.

Specific examples of preferred compounds of the present invention are at least one member selected from the group consisting of 1-[2-(acetylthio) ethyl]-1-(2-cyclohexylethyl)-3-[2-(1-pyrrolidinyl) ethyl] urea, 1-[2-(acetylthio) ethyl-1-(2cyclohexylethyl)-3-[3-(1-pyrrolidinyl) propyl] urea, 1-[2-(acetylthio) ethyl]-1-(2-cyclohexylethyl)-3-[3-(1-piperidyl) propyl] urea, 1-[2-(acetylthio) ethyl]-3-[(1S)-1-benzyl-2-(4-methylpiperazin-1-yl) ethyl]-1-phenethyl urea, 1-[2-(acetylthio) ethyl]-1-(2-cyclohexylethyl)-—³-[2-(1-homopiperidyl) ethyl] urea, 1-[2-(acetylthio) ethyl]-1-(2-cyclohexylethyl)-3-[2-(1,2,5,6-tetrahydropyridin-1-yl) ethyl] urea, 1-[2-(acetylthio) ethyl]-1-(2-cyclohexylethyl)-3-[[(2RS)-1-ethyl-2-pyrrolidinyl] methyl] urea, 1-[2-(acetylthio) ethyl]-1-(2-cyclohexylethyl)-3-[2-(1-piperidyl) ethyl] urea, 1-[2-(acetylthio) ethyl]-1-(2-cyclohexylethyl)-3-[2-[4-(dimethylamino)-1-piperidyl]ethyl] urea, 1-[2-(acetylthio) ethyl]-1-(2-cyclohexylethyl)-3-[(1-methyl-4-piperidyl) methyl) urea and 1-(2-cyclohexyl-ethyl)-1-[2-(methylthio) ethyl]-3-[2-(1-piperidyl) ethyl] urea, as well as pharmaceutically acceptable salts thereof.

The salts used in the present invention are not restricted to any particular one inasmuch as they are pharmaceutically acceptable salts and examples thereof are salts with inorganic acids such as hydrochloric acid, nitric acid and sulfuric acid, salts with organic acids such as acetic acid, fumaric acid, maleic acid, tartaric acid and citric acid. And salts with alkali metals or alkaline earth metals such as sodium, potassium and calcium. In addition, the compound of the present invention may form a geometrical isomer or an optical isomer, these isomers likewise fall within the scope of the present invention. Moreover, the compound of the present invention may be in the form of a hydrate.

The compounds of the present invention represented by the general formula I may be synthesized by, for instance, the following representative. method or those similar to the same.

Formula [III] and a thio derivative [VIII] are condensed together according to the Mitsunobu reaction to give a compound represented by the general formula I according to the present invention.

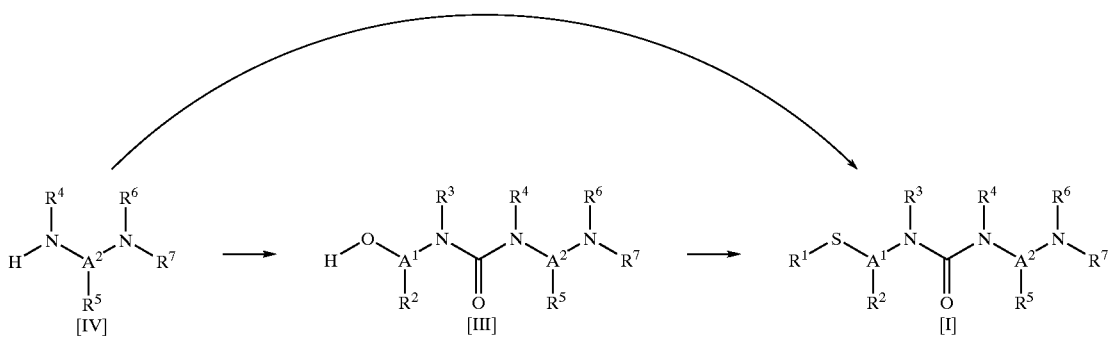

The foregoing method includes the following two synthetic methods A and B.

Synthetic Method A: Compounds of Formula [IV] →Compounds of Formula [III]→Compounds of Formula I Synthetic Method B: Compounds of Formula [IV] →Compounds of Formula I These synthetic methods will be detailed below.

Synthetic Method A:

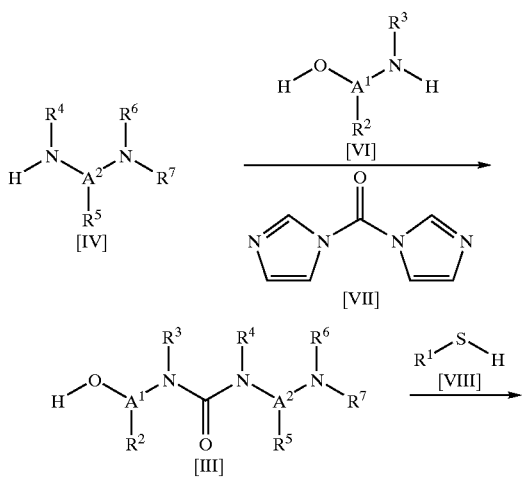

A compound of Formula [IV] is reacted with an aminoalcohol derivative [VI] in the presence of a condensation agent (such as 1,1'-carbonyl diimidazole [VII]) to give a compound of Formula [III] and then the resulting compound of Synthetic Method B:

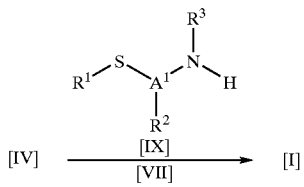

A compound of Formula [IV] is reacted with a compound of Formula [IX] in the presence of a condensation agent (such as 1,1'-carbonyl diimidazole [VII]) to directly give a compound represented by the general formula I according to the present invention. In this respect, the compound of Formula [IV] and the compound of Formula [IX] can easily be synthesized according to the method disclosed in Japanese Patent Application Ser. No. Hei 10-79154.

The compounds of the foregoing Formula [III] are novel compounds and useful intermediates for use in the preparation of the compounds represented by the general formula I according to the present invention. In the foregoing formula, $R^2$, $R^3$, $R^4$, $R^5$, $R^6$, $R^7$, $A^1$ and $A^2$ are the same as those defined above in connection with the general formula I and preferred examples thereof are likewise the same as those described above in connection with the general formula I.

In the foregoing synthetic methods, if a reactant includes a thiol, hydroxyl, amino group or a nitrogen atom as a member of a heterocyclic ring, in the molecule, these groups or atom may, if necessary, be protected with appropriate protective groups and these protective groups may be removed after the completion of the reaction according to the usual methods. In addition, if a reactant includes a carboxyl group in the molecule, the carboxyl group may, if necessary, be esterified and the ester may be converted into a carboxylic acid through hydrolysis.

In the compound of the present invention, if $R^2$ is linked with the sulfur atom adjacent to $A^1$ to form a thiolactone ling, the compound of the present invention can likewise be prepared according to the following method in addition to the aforementioned route. More specifically, if $R^2$ represents a carboxyl group and $R^1$ represents a hydrogen atom in Formula [I], the thiolactone ling may be synthesized by condensing these groups.

The compounds prepared according to the foregoing method may be converted into the corresponding salts detailed above according to the usual methods.

The TNF-α production inhibitory action of the compounds according to the present invention will be described in the following section entitled "Pharmacological Tests". In the tests, the inhibitory effects of the compounds on the release of TNF-α induced by the stimulation of lipopolysaccharide (LPS) were investigated in vitro and in vivo. As a result, it was found that the compounds of the present invention clearly showed an excellent TNF-α production inhibitory action.

It has been known that the productivity of TNF-α is closely related to the crisis of, for instance, autoimmune diseases such as articular rheumatism, Crohn's disease and systemic erythematodes, dyscrasia, acute infectious diseases, allergy, fever, anemia and diabetes. Accordingly, compounds having an effect of inhibiting the production thereof such as those of the present invention would be expected to be useful as drugs for treating wide variety of these diseases.

The compound of the present invention may be administered through oral and parenteral routes. Examples of the dosage forms of the compounds include tablets, capsules, granules, powders and injections and they can be formed into these pharmaceutical preparations using techniques currently used in the art. For instance, oral drugs such as tablets, capsules, granules and powders may be prepared by, if necessary, incorporating, into the compound, a thickening agent such as lactose, crystalline cellulose, starch and vegetable oils, a lubricant such as magnesium stearate and talc, a binder such as hydroxypropyl cellulose and polyvinyl pyrrolidone, a disintegrator such as carboxymethyl cellulose, calcium and low substituted hydroxypropylmethyl cellulose, a coating agent such as hydroxypropylmethyl cellulose, macrogol and silicone resin, and a film-forming agent such as gelatin film.

The dose of the compound of the present invention may appropriately be selected depending on, for instance, the symptoms and age of each particular patient and the dosage forms, but it usually ranges from 0.1 to 5000 mg, preferably 1 to 1000 mg per day for the oral administration, which may be administered at a time or over several times in portions.

Preparation Examples of the compounds of the present invention, Examples of pharmaceutical preparations and the results of Pharmacological Tests will be given below, but they are given for deepening the understanding of the present invention and never limit the scope of the present invention at all.

[PREPARATION EXAMPLES]

Reference Example 1

(1S)-1-Benzyl-2-(4-methylpiperazin-1-yl) ethylamine (Reference Compound 1-1)

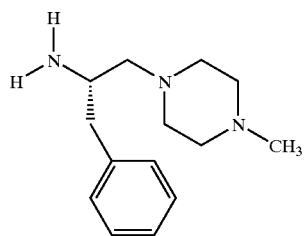

Lithium aluminum hydride (531 mg) was suspended in anhydrous ether (14 ml) with ice cooling in the nitrogen gas atmosphere and then a solution of 1-[(2S)-2-amino-3-phenylpropionyl]-4-methylpiperazine (1.48 g) in anhydrous tetrahydrofuran (7 ml) was dropwise added to the resulting suspension. The reaction system was stirred at room temperature for 4 hours. Ethyl acetate was gradually dropwise added to the reaction liquid with ice cooling till the reaction system did not undergo foaming any more. Then a 2N sodium hydroxide aqueous solution was added to the reaction system and the resulting mixture was extracted with chloroform. The resulting organic phase was dried over anhydrous sodium sulfate and then concentrated under reduced pressure to give the title compound (Reference Compound 1-1, 1.25 g).

(Reference Compound 1-1)

[α]D20+9.1° (c=1.0, chloroform)

IR (Film, cm$^{-1}$): 3288, 2936, 2795, 1601, 1495, 1455, 1374, 1283, 1166 and 1013

Reference Example 2

3-(1-Pyrrolidinyl) propylamine (Reference Compound 2-1)

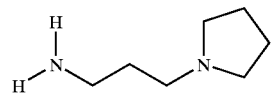

N-[3-(1-Pyrrolidinyl) propyl] phthalimide (729 mg) and hydrazine monohydrate (284 mg) were dissolved in methanol (9 ml) and the resulting solution was refluxed with heating for 2 hours. After cooling, the reaction solution was concentrated under reduced pressure followed by addition of a 4N sodium hydroxide aqueous solution to the resulting residue and extraction thereof with chloroform. The resulting organic phase was dried over anhydrous sodium sulfate and concentrated under reduced pressure to give the title compound (Reference Compound 2-1, 216 mg).

(Reference Compound 2-1)

IR (Film, cm$^{-1}$): 3283, 2932, 2874, 2786, 1584, 1460, 1386, 1350, 1293, 1203, 1145 and 877

The procedures similar to those used in Reference Example 2 were repeated to give the following compounds.

3-(1-Piperidyl) propylamine (Reference Compound 2-2)

IR (Film, cm$^{-1}$): 3286, 2933, 2853, 1592, 1469, 1442 and 1124

[(3RS)-1-methyl-3-piperidyl] methylamine (Reference Compound 2-3)

IR (Film, cm$^{-1}$): 3286, 2931, 2848, 2775, 1655, 1598, 1465, 1446 and 1094

(2RS)-2-(t-Butyldimethyl siloxy)-3-(4-methylpiperazin-1-yl) propylamine (Reference Compound 2-4)

mp 35.0~40.0° C.

IR (KBr, cm$^{-1}$): 3363, 3290, 2934, 2855, 2800, 1594, 1459, 1359, 1284, 1247, 1166, 1115, 1012, 965, 877, 834 and 776

Reference Example 3

2-(1-Homopiperidyl) ethylamine di-hydrochloride (Reference Compound 3-1)

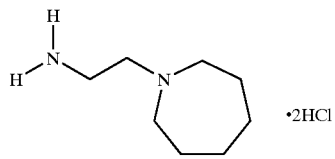

A 4N solution of hydrogen chloride in ethyl acetate was added to a solution of N-(t-butoxycarbonyl)-2-(1-homopiperidyl) ethylamine (2.31 g) in ether (5 ml) in the nitrogen gas atmosphere. After stirring the resulting mixture at room temperature for 15 minutes, the precipitates were filtered to give the title compound. (Reference Compound 3-1, 1.59 g) in the form of crystals.

(Reference Compound 3-1)

mp 162~173° C.

IR (KBr, $cm^{-1}$): 3510, 3384, 2938, 2624, 2045, 1604, 1572 and 1463

The procedures similar to those used in Reference Example 3 were repeated to obtain the following compounds.

2-(4-Methyl-1-piperidyl) ethylamine di-hydrochloride (Reference Compound 3-2)

mp 155~161° C.

IR (KBr, $cm^{-1}$): 3477, 3395, 2956, 2630, 1600, 1566, 1502, 1455, 1054 and 962

2-[4-(Dimethylamino)-1-piperidyl] ethylamine tri-hydrochloride (Reference Compound 3-3)

mp: not less than 250° C.

IR (KBr, $cm^{-1}$): 3566, 2991, 2546, 1578, 1515 and 1468

2-(3-Pyrrolin-1-yl) ethylamine di-hydrochloride (Reference Compound 3-4)

IR (Film, $cm^{-1}$): 3400, 2958, 1607, 1454, 1040 and 694

2-(1,2,5,6-Tetrahydropyridin-1-yl) ethylamine di-hydrochloride (Reference Compound 3-5)

mp: 82~98° C.

IR (KBr, $cm^{-1}$): 3450, 2981, 2587, 1596, 1477, 1035 and 939

2-(1,2,3,4-Tetrahydroisoquinolin-2-yl) ethylamine di-hydrochloride (Reference Compound 3-6)

IR (Film, $cm^{-1}$): 3396, 2960, 1608, 1455, 1161, 1026 and 754

Reference Example 4

[1-(Benzyloxycarbonyl)-4-piperidyl] methylamine hydrochloride (Reference Compound 4-1)

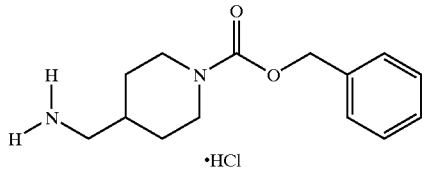

To a solution of 4-aminomethyl piperidine (7.19 g) in anhydrous methylene chloride (80 ml), there was dropwise added a solution of benzyloxycarbonyl chloride (3.0 ml) in anhydrous methylene chloride (25 ml) under a nitrogen gas atmosphere while cooling with dry ice-methanol. After the completion of the dropwise addition, the resulting mixture was stirred while cooling with dry ice-methanol for 20 minutes and then stirred at room temperature for additional 2 hours. The reaction solution was concentrated under reduced pressure and ether and a citric acid solution were added to the resulting residue. The resulting aqueous phase was washed twice with ether. After addition of chloroform to the aqueous phase, sodium carbonate was added thereto at room temperature with stirring to make the aqueous phase basic. Separately, the resulting organic phase was washed with saturated sodium chloride aqueous solution, dried over anhydrous magnesium sulfate and then concentrated under reduced pressure. The resulting oily product was dissolved in ether and a 4N hydrogen chloride solution in ethyl acetate (10 ml) was added to the ether solution with ice cooling. The resulting precipitates were filtered off to thus give the title compound (Reference Compound 4-1, 1.86 g) in the form of crystals.

(Reference Compound 4-1)

mp: 130.0~135.0° C.

IR (KBr, $cm^{-1}$): 2926, 1699, 1604, 1468, 1436, 1366, 1282, 1245 and 1170

Reference Example 5

2-[4-(t-Butyldimethyl siloxy)-1-piperidyl] ethylamine (Reference Compound 5-1)

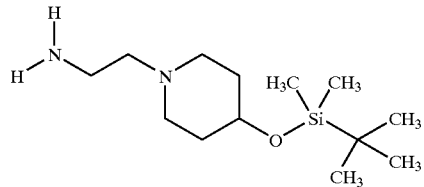

To a solution of N-(benzyloxycarbonyl)-2-[4-(t-butyldimethyl siloxy)-1-piperidyl] ethylamine (1.47 g) in tetrahydrofuran (37 ml), there was added 20% palladium hydroxide-on-carbon (100 mg). The resulting mixture was stirred over 2 days under a hydrogen gas atmosphere. The mixture was filtered through celite to remove the palladium hydroxide-on-carbon and the resulting filtrate was concentrated under reduced pressure. The resulting oily product was purified through the silica gel column chromatography to thus give the title compound (Reference Compound 5-1, 0.28 g).

(Reference Compound 5-1)

IR (Film, $cm^{-1}$): 3788, 3357, 2950, 2857, 1582, 1551, 1531, 1470, 1254, 1098, 874 and 835

The procedures similar to those used in Reference Example 5 were repeated to prepare the following compound.

2-[(2S)-2-(t-Butoxydimethyl siloxymethyl)-1-pyrrolidinyl] ethylamine (Reference Compound 5-2)

$[\alpha]D20$: −33.7° (c=1.0, methanol)

IR (Film, $cm^{-1}$): 2952, 1471, 1254, 1099 and 839

Example 1

1-(2-Cyclohexylethyl)-1-(2-hydroxyethyl)-3-[2-(1-piperidyl)ethyl]-urea (Compound 1-1)

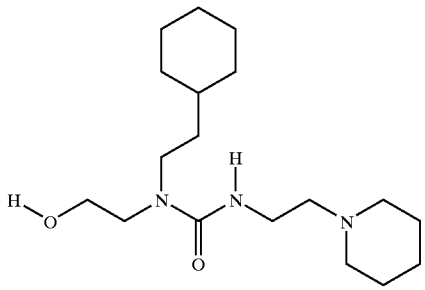

1,1'-Carbonyldiimidazole (740 mg) was dissolved in a solution of 2-(1-piperidyl) ethylamine (0.50 ml) in anhydrous tetrahydrofuran (18 ml) under the nitrogen gas atmosphere and then the mixture was stirred at room temperature for 20 minutes. N-(2-Hydroxyethyl)-2-cyclohexylethylamine hydrochloride (875 mg) was added to the reaction solution and the mixture was refluxed with heating for 3 hours. Ether was added to the reaction solution with ice cooling, the resulting mixture was washed with saturated aqueous sodium hydrogen carbonate solution and saturated sodium chloride aqueous solution in this order, dried over anhydrous magnesium sulfate and then concentrated under reduced pressure. The resulting oily product was purified through the silica gel column chromatography to give the title compound (Compound 1-1, 1.01 g).

(Compound 1-1)

IR (Film, cm$^{-1}$): 3342, 2923, 2850, 1626, 1536, 1127 and 1064

The procedures similar to those used in Example 1 were repeated to give the following compounds.

1-(2-Cyclohexylethyl)-1-(2-hydroxyethyl)-3-[2-(1-pyrrolidinyl) ethyl] urea (Compound 1-2)

IR (Film, cm$^{-1}$): 3351, 2922, 2851, 1747, 1633, 1538, 1447, 1408, 1372, 1268, 1147, 1055 and 754

1-(2-Cyclohexylethyl)-1-(2-hydroxyethyl)-3-[3-(1-pyrrolidinyl) propyl] urea (Compound 1-3)

IR (Film, cm$^{-1}$): 3330, 2922, 2850, 2799, 1626, 1537, 1448, 1406, 1372, 1270, 1143, 1056, 872 and 764

1-(2-Cyclohexylethyl)-1-(2-hydroxyethyl)-3-[3-(1-piperidyl) propyl] urea (Compound 1-4)

IR (Film, cm$^{-1}$): 3324, 2924, 2851, 1624, 1538, 1447, 1124 and 1062

1-(2-Cyclohexylethyl)-1-(2-hydroxyethyl)-3-[2-(4-methylpiperazin-1-yl)-ethyl] urea (Compound 1-5)

IR (Film, cm$^-$): 3353, 2922, 2849, 1629, 1536, 1448, 1285, 1165, 1053, 1012 and 753

1-[(1S)-1-Benzyl-2-(4-methylpiperazin-1-yl) ethyl]-3-(2-hydroxyethyl)-3-phenethyl urea (Compound 1-6)

[α]D20: +9.8° (c=0.94, chloroform)

IR (Film, cm$^{-1}$): 3305, 2938, 2805, 1630, 1496, 1454, 1405, 1373, 1285, 1167 and 1011

1-(2-Cyclohexylethyl)-1(2-hydroxyethyl)-3-[2-(4-morpholinyl) ethyl] urea (Compound 1-7)

mp: 98.5~100.7° C.

IR (KBr, cm$^{-1}$): 3356, 3119, 2920, 2846, 1640, 1538, 1494, 1298, 1119, 1054, 1007, 864 and 764

1-(2-Cyclohexylethyl)-1-(2-hydroxyethyl)-3-[3-(4-morpholinyl) propyl] urea (Compound 1-8)

IR (Film, cm$^{-1}$): 3325, 2922, 2851, 1626, 1537, 1118 and 1066

1-(2-Cyclohexylethyl)-1-(2-hydroxyethyl)-3-[2-(1-homopiperidyl) ethyl]-urea (Compound 1-9)

IR (Film, cm$^{-1}$): 3338, 2922, 2851, 1626, 1537, 1448, 1268, 1167, 1132 and 1054

1-(2-Cyclohexylethyl)-1-(2-hydroxyethyl)-3-[2-(4-methyl-1-piperidyl) ethyl]-urea (Compound 1-10)

IR (Film, cm$^{-1}$): 3339, 2922, 2850, 1626, 1536, 1448, 1261, 1064 and 753

1-(2-Cyclohexylethyl)-1-(2-hydroxyethyl)-3-[2-[4-(dimethylamino)-1-piperidyl] ethyl] urea (Compound 1-11)

IR (Film, cm$^{-1}$): 3118, 2923, 2851, 1626, 1538, 1448, 1256 and 1063

1-(2-Cyclohexylethyl)-1-(2-hydroxyethyl)-3-[2-(3-pyrrolin-1-yl) ethyl] urea (Compound 1-12)

IR (Film, cm$^{-1}$): 3340, 2922, 2850, 1628, 1540, 1448, 1270 and 1055

1-(2-Cyclohexylethyl)-1-(2-hydroxyethyl)-3-[2-(1,2,5,6-tetrahydropyridin-1-yl) ethyl] urea (Compound 1-13)

IR (Film, cm$^{-1}$): 3350, 2922, 2850, 1629, 1536, 1268, 1054 and 754

1-(2-Cyclohexylethyl)-1-(2-hydroxyethyl)-3-[2-(1,2,3,4-tetrahydroisoquinolin-2-yl) ethyl] urea (Compound 1-14)

IR (Film, cm$^{-1}$): 3354, 2922, 2850, 1633, 1520 and 751

1-(2-Cyclohexylethyl)-1-(2-hydroxyethyl)-3-[2-[(2RS)-1-methyl-2-pyrrolidinyl] ethyl] urea (Compound 1-15)

IR (Film, cm$^{-1}$): 3329, 2922, 2850, 2786, 1626, 1536, 1448, 1407, 1375, 1227, 1124 and 1055

1-(2-Cyclohexylethyl)-1-(2-hydroxyethyl)-3-[[(3RS)-1-methyl-3-piperidyl]-methyl]urea (Compound 1-16)

IR (Film, cm$^{-1}$): 3326, 2922, 2850, 2782, 1626, 1538, 1448, 1268 and 753

1-(2-Cyclohexylethyl)-1-(2-hydroxyethyl)-3-[[(2RS)-1-ethyl-2-pyrrolidinyl]-methyl]urea (Compound 1-17)

IR (Film, cm$^{-1}$): 3338, 2923, 2851, 1633, 1538, 1448, 1406, 1374, 1246, 1056 and 754

1-[[1-(Benzyloxycarbonyl)-4-piperidyl]methyl]-3-(2-cyclohexylethyl)-3-(2-hydroxy-ethyl) urea (Compound 1-18)

mp: 94.5–95.5° C.

IR (KBr, cm$^{-1}$): 3247, 2923, 2850, 1700, 1618, 1557, 1477, 1452, 1435, 1365, 1318, 1282, 1254, 1244, 1220 and 1149

1-[(2RS)-2-(t-Butyldimethyl siloxy)-3-(4-methyl-1-piperazinyl) propyl]-3-(2-cyclohexyl-ethyl)-3-(2-hydroxyethyl) urea (Compound 1-19)

IR (Film, cm$^{-1}$): 3340, 2926, 2852, 2803, 1633, 1530, 1460, 1405, 1360, 1283, 1251, 1167, 1097, 1012, 836, 810, 777 and 754

1-[2-[4-(t-Butyldimethyl siloxy)-1-piperidyl] ethyl]-3-(2-cyclohexylethyl)-3-(2-hydroxy- ethyl) urea (Compound 1-20)

IR (Film, cm$^{-1}$): 3339, 2926, 2853, 1630, 1536, 1471, 1449, 1407, 1375, 1360, 1252, 1098 and 1056

1-[2-[(2S)-2-[(t-Butyldimethyl siloxy) methyl]-1-pyrrolidinyl]ethyl]-3-(2-cyclohexyl-ethyl)-3-(2-hydroxyethyl) urea (Compound 1-21)

IR (Film, cm$^{-1}$): 3340, 2925, 2853, 1631, 1530, 1471, 1448, 1255 and 1088

1-[2-(1-Adamantyl) ethyl] -1-(2-hydroxyethyl)-3-[2-(1-piperidyl) ethyl]urea (Compound 1-22)

Example 2

1-(2-Cyclohexylethyl)-1-(2-hydroxyethyl)-3-[(1-methyl-4-piperidyl) methyl] urea (Compound 2-1)

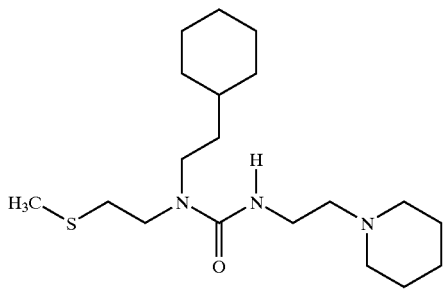

1-(2-Cyclohexylethyl)-1-(2-hydroxyethyl)-3-[2-(1-piperidyl) ethyl]urea (Compound 1-1, 0.94 g) and triphenyl phosphine (1.52 g) were dissolved in anhydrous tetrahydrofuran (14 ml) in the nitrogen gas atmosphere and the resulting solution was stirred for 30 minutes under sodium chloride-ice cooling. There were dropwise added, to the cooled solution, in order, diisopropyl azodicarboxylate (1.14 ml) and a solution of thioacetic acid (0.44 g) in anhydrous tetrahydrofuran (1 ml), while maintaining the temperature of the solution to not higher than 5° C. After stirring the solution for one hour, a saturated aqueous solution of sodium hydrogen carbonate (40 ml) was added to the reaction solution and then the mixture was extracted with ether. The resulting organic phase was washed with saturated aqueous sodium chloride aqueous solution, dried over anhydrous magnesium sulfate and then concentrated under reduced pressure. The resulting oily product was purified through the silica gel column chromatography to thus give the title compound (Compound 3-1).

(Compound 3-1)

IR (Film, cm$^{-1}$): 3392, 2923, 2850, 1692, 1633, 1532, 1250 and 1222

The procedures similar to those used in Example 3 were repeated to obtain the following compounds.

1-[2-(Acetylthio) ethyl]-1-(2-cyclohexylethyl)-3-[2-(1-pyrrolidinyl) ethyl]-urea (Compound 3-2)

IR (Film, cm$^{-1}$): 3350, 2923, 2851, 2794, 1693, 1634, 1537, 1447, 1404, 1354, 1294, 1138, 951 and 753

1-[2-(Acetylthio) ethyl]-1-(2-cyclohexylethyl)-3-[3-(1-pyrrolidinyl) propyl]-urea (Compound 3-3)

IR (Film, cm$^{-1}$): 3324, 2922, 2598, 2484, 1691, 1633, 1531, 1448, 1295, 1135, 951 and 753

1-[2-(Acetylthio) ethyl]-1-(2-cyclohexylethyl)-3-[3-(1-piperidyl) propyl]urea (Compound 3-4)

IR (Film, cm$^{-1}$): 3350, 2923, 2851, 1693, 1632, 1537, 1446 and 1133

1-[2-(Acetylthio) ethyl]-1-(2-cyclohexylethyl)-3-[2-(4-methylpiperazin-1-yl) ethyl]urea (Compound 3-5)

IR (Film, cm$^{-1}$): 3396, 2923, 2848, 2795, 1691, 1636, 1535, 1450, 1293, 1165, 1014, 950 and 760

1-[2-(Acetylthio) ethyl]-3-[(1S)-1-benzyl-2-(4-methylpiperazin-1-yl) ethyl]-1-phenethyl urea (Compound 3-6)

[α] D20: −12.2° (c=1.0, methanol)

IR (Film, cm$^{-1}$): 3391, 2936, 2796, 1681, 1643, 1530, 1496, 1455, 1286, 1140, 1013, 750 and 701

1-12-(Acetylthio) ethyl]-1-(2-cyclohexylethyl)-3-[2-(4-morpholinyl) ethyl]-urea (Compound 3-7)

IR (Film, cm$^{-1}$): 3400, 2921, 2850, 1691, 1639, 1531, 1447, 1356, 1296, 1140, 1118, 949 and 865

1-[2-(Acetylthio) ethyl]-1-(2-cyclohexylethyl)-3-[3-(4-morpholinyl) propyl]-urea (Compound 3-8)

IR (Film, cm$^{-1}$): 3360, 2922, 2851, 1693, 1632, 1532, 1293 and 1118

1-[2-(Acetylthio) ethyl]-1-(2-cyclohexylethyl)-3-[2-(1-homopiperidyl) ethyl]-urea (Compound 3-9)

IR (Film, cm$^{-1}$): 3367, 2922, 2850, 1693, 1634, 1532, 1448, 1402, 1355, 1294, 1219 and 1135

1-[2-(Acetylthio) ethyl]-1-(2-cyclohexylethyl)-3-[2-(4-methyl-1-piperidyl)-ethyl] urea (Compound 3-10)

IR (Film, cm$^{-1}$): 3400, 2922, 2850, 1693, 1633, 1531, 1448, 1293, 1132, 951 and 753

1-[2-(Acetylthio) ethyl]-1-(2-cyclohexylethyl)-3-[2-[4-(dimethylamino)-1-piperidyl] ethyl] urea (Compound 3-11)

1-[2-(Acetylthio) ethyl]-1-(2-cyclohexylethyl)-3-[2-(3-pyrrolin-1-yl) ethyl]-urea (Compound 3-12)

IR (Film, cm$^{-1}$): 3368, 2923, 2851, 2789, 1692, 1634, 1535, 1137 and 754

1-[2-(Acetylthio) ethyl]-1-(2-cyclohexylethyl)-3-[2-(1,2,5,6-tetrahydropyridin-1-yl) ethyl] urea (Compound 3-13)

IR (Film, cm$^{-}$): 3400, 2922, 2850, 1691, 1637, 1531, 1137 and 754

1-[2-(Acetylthio) ethyl]-1-(2-cyclohexylethyl)-3-[2-(1,2,3,4-tetrahydroisoquinolin-2-yl) ethyl] urea (Compound 3-14)

IR (Film, cm$^{-1}$): 3398, 2922, 2850, 1692, 1644, 1531, 1136 and 747

1-[2-(Acetylthio) ethyl]-1-(2-cyclohexylethyl)-3-[2-[(2RS)-1-methyl-2-pyrrolidinyl] ethyl]urea (Compound 3-15)

IR (Film, cm$^{-1}$): 3350, 2922, 2850, 2780, 1694, 1633, 1538, 1448, 1355, 1295, 1214, 1136 and 1019

1-[2-(Acetylthio) ethyl]-1-(2-cyclohexylethyl)-3-[[(3RS)-1-methyl-3-piperidyl] methyl] urea (Compound 3-16)

IR (Film, cm$^{-1}$): 3350, 2923, 2850, 2777, 1693, 1632, 1537, 1448, 1293, 1139, 950 and 753

1-[2-(Acetylthio) ethyl]-1-(2-cyclohexylethyl)-3-[[(2RS)-1-ethyl-2-pyrrolidinyl] methyl] urea (Compound 3-17)

IR (Film, cm$^{-1}$): 3368, 2923, 2851, 1693, 1640, 1530, 1448, 1402, 1355, 1293, 1220, 1137, 950 and 753

1-[2-(Acetylthio) ethyl]-1-(2-cyclohexylethyl)-3-[(1-methyl-4-piperidyl)-methyl] urea (Compound 3-18)

1-[2-(Acetylthio) ethyl]-3-[(2RS)-2-(t-butyldimethyl siloxy)-3-(4-methyl-1-piperazinyl) propyl]-1-(2-cyclohexylethyl) urea (Compound 3-19)

IR (Film, cm$^{-1}$): 3411, 2926, 2852, 2795, 1693, 1644, 1520, 1456, 1403, 1359, 1294, 1250, 1166, 1111, 1014, 836 and 777

1-[2-(Acetylthio) ethyl]-3-[2-[4-(t-butyldimethyl siloxy)-1-piperidyl]ethyl]-1-(2-cyclo-hexylethyl) urea (Compound 3-20)

IR (Film, cm$^{-1}$): 3407, 2926, 2854, 1692, 1640, 1531, 1448, 1293, 1100 and 1056

1-[2-(Acetylthio) ethyl]-3-[2-[(2S)-2-[(t-butyldimethyl siloxy) methyl]-1-pyrrolidinyl]ethyl]-1-(2-cyclohexylethyl) urea (Compound 3-21)

[α] D20: −23.8° (c=1.0, methanol)

IR (Film, cm$^{-1}$): 3401, 2925, 2854, 1692, 1541, 1530, 1448, 1357, 1292, 1253, 1103 and 1006

1-[2-(Acetylthio) ethyl]-1-[2-(1-adamantyl) ethyl]-3-[2-(1-piperidyl) ethyl]-urea (Compound 3-22)

Example 4

1-(2-Cyclohexylethyl)-1-[2-(methylthio) ethyl]-3-[2-(1-piperidyl)-ethyl]urea (Compound 4-1):

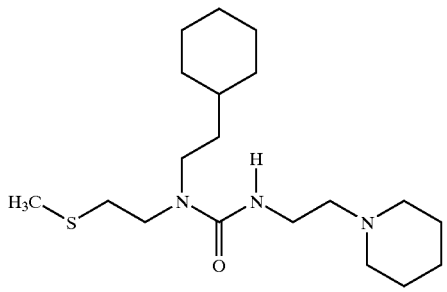

To a solution of 2-(1-piperidyl) ethylamine (151 mg) in anhydrous tetrahydrofuran (5.9 ml), there was added 1,1'-carbonyl diimidazole (228 mg) in a nitrogen gas atmosphere and the resulting mixture was stirred at room temperature for 15 minutes. Then 2-cyclohexyl-N-[2-(methylthio) ethyl]-ethylamine hydrochloride (309 mg) was added to the foregoing mixture and the resulting mixture was refluxed with heating for 45 minutes. Ethyl acetate was added to the reaction solution with ice cooling, followed by washing the reaction solution with saturated aqueous solution of sodium hydrogen carbonate and then with saturated sodium chloride aqueous solution, drying over anhydrous sodium sulfate and concentration under reduced pressure. The resulting oily product was purified by the silica gel column chromatography to thus give the title compound (Compound 4-1).

Example 5

1-[2-(Acetylthio) ethyl]-1-(2-cyclohexylethyl)-3-[(2RS)-2-hydroxy-3-(4-methyl-1-piperadinyl) propyl] urea (Compound 5-1)

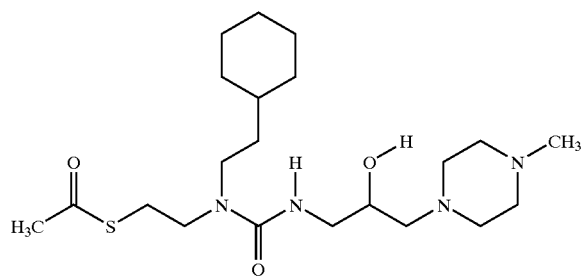

1-[2-(Acetylthio) ethyl]-3-[(2RS)-2-(t-butyldimethyl siloxy)-3-(4-methyl-1-piperazinyl)propyl]-1-(2-cyclohexylethyl) urea (Compound 3-19, 748 mg) was dissolved in anhydrous tetrahydrofuran (1.4 ml) in the nitrogen gas atmosphere, followed by the addition of a 1M solution of fluorinated tetra-n-butyl ammonium fluoride in tetrahydrofuran (1.45 ml) to the resulting solution with stirring at room temperature and stirring the mixture over 2.5 days. Saturated aqueous solution of sodium hydrogen carbonate was added to the reaction solution and the resulting mixture was extracted with ethyl acetate. The resulting organic phase was washed with saturated aqueous solution of sodium hydrogen carbonate and then saturated sodium chloride aqueous solution, dried over anhydrous sodium sulfate and then concentrated under reduced pressure. The resulting oily product was purified by the silica gel column chromatography to thus give the title compound (Compound 5-1, 89 mg).

(Compound 5-1)

IR (Film, cm$^{-1}$): 3350, 2923, 1691; 1630, 1532, 1449, 1355, 1292, 1244, 1166, 1139, 1104, 1012, 950, 818 and 755

The procedures similar to those used in Example 5 were repeated to give the following compounds.

1-[2-(Acetylthio) ethyl]-1-(2-cyclohexylethyl)-3-[2-(4-hydroxy-1-piperidyl)-ethyl]urea (Compound 5-2)

IR (Film, cm$^{-1}$): 3388, 2923, 2850, 1693, 1632, 1537, 1448, 1406, 1356, 1294, 1137 and 1074

1-[2-(Acetylthio) ethyl]-1-(2-cyclohexylethyl)-3-[2-[(2S)-2-(hydroxymethyl)-1-pyrrolidinyl]ethyl]urea (Compound 5-3)

[α]D20: −23.2° (c=1.0, methanol)

IR (Film, cm$^{-1}$): 3390, 2922, 2850, 1692, 1631, 1536, 1448, 1406, 1355, 1294, 1246, 1137 and 1042

Example 6

1-[2-(Acetylthio) ethyl]-1-(2-cyclohexylethyl)-3-[2-(1-piperidyl)-ethyl]urea hydrochloride (Compound 6-1).

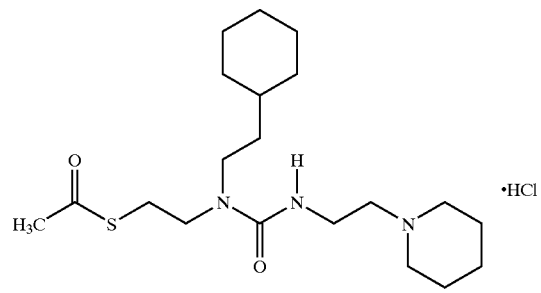

To a solution of 1-[2-(acetylthio) ethyl]-1-(2-cyclohexylethyl)-3-[2-(1-piperidyl) ethyl] urea (Compound 3-1, 618 mg) in ether, there was added a 4N hydrogen chloride solution in ethyl acetate (0.4 ml). The resulting precipitates were filtered off to give the title compound (Compound 6-1, 401 mg) in the form of crystals.

(Compound 6-1)

mp: 131.5~133.5° C.

IR (KBr, cm$^{-1}$): 3391, 2923, 2852, 2619, 2585, 2498, 2409, 1684, 1633, 1538, 1485, 1453, 1414, 1403, 1354, 1297, 1247, 1222, 1197, 1137 and 1112

The procedures similar to those used in Example 6 were repeated to prepare the following compounds.

1-[2-(Acetylthio) ethyl]-1-(2-cyclohexylethyl)-3-[2-[4-(dimethylamino)-1-piperidyl]ethyl]urea di-hydrochloride (Compound 6-2)

mp: 170° C. (decomposed)

IR (KBr, cm$^{-1}$): 3442, 2922, 2851, 2653, 1694, 1631, 1536, 1449, 1409 and 1294

1-[2-(Acetylthio) ethyl]-1-(2-cyclohexylethyl)-3-[(1-methyl-4-piperidyl)-methyl]urea hydrochloride (Compound 6-3)

mp: 178.5~179.3° C.

IR (KBr, cm$^{-1}$): 3331, 2922, 2850, 2692, 2576, 2528, 1699, 1630, 1539, 1481, 1449, 1432, 1409, 1354, 1314, 1292, 1255, 1214 and 1136

1-(2-Cyclohexylethyl)-1-[2-(methylthio) ethyl]-3-[2-(1-piperidyl) ethyl]urea hydrochloride (Compound 6-4)

mp: 68.9~70.8° C.

IR (KBr, cm$^{-1}$): 3384, 3298, 2924, 2851, 2641, 2585, 2551, 1657, 1626, 1560, 1496, 1448, 1408, 1360, 1325, 1298, 1254, 1224, 1204, 1185, 1152, 1101 and 1083

[Examples of Pharmaceutical Preparations]

Examples of general formulations of orally administered drugs and injections containing the compounds of the present invention will be given below.

| 1) Tablets: Formulation 1 (per 100 mg) | |
|---|---|
| Compound of the Present Invention | 1 mg |
| Lactose | 66.4 mg |
| Corn Starch | 20 mg |
| Calcium Carboxymethylcellulose | 6 mg |
| Hydroxypropylcellulose | 4 mg |
| Magnesium Stearate | 0.6 mg |

Each tablet having the foregoing formulation was coated with 2 mg of a coating agent (for instance, a currently used coating agent such as hydroxypropylmethylcellulose, macrogol or a silicone resin) to thus give a desired coated tablet (the tablets having the following formulations were likewise be prepared by the same method). In addition, desired tablets can be prepared by appropriately and variously changing the amounts of the compound according to the present invention and various additives.

| 2) Capsules: Formulation 1 (per 150 mg) | |
|---|---|
| Compound of the Present Invention | 5 mg |
| Lactose | 145 mg |

Desired capsules can be prepared by appropriately and variously changing the mixing ratio of the compound of the present invention to lactose.

| 3) Injections: Formulation 1 (per 10 ml) | |
|---|---|
| Compound of the Present Invention | 10 to 100 mg |
| Sodium Chloride | 90 mg |
| Sodium Hydroxide (or Hydrochloric Acid) | Sufficient Quantity |
| Sterilized and Purified Water | Sufficient Quantity |

Desired injections can be prepared by appropriately and variously changing the mixing ratio of the compound of the present invention to the additives.

[Pharmacological Tests]

Each candidate compound was inspected for the effect of inhibiting TNF-α production induced by the stimulation with lipopolysaccharide (LPS), by an in vitro or in vivo test according to the method proposed by McGeehan et al. (Nature, 1994, 370:558–561).

1) In Vitro Test

The test was carried out by, determining the amount of TNF-α produced by the human monocyte strain THP-1 induced by the stimulation with LPS.

The culture medium used in this test was RPMI 1640 culture medium supplemented wiTNFetal calf serum (10%), L-glutamine (2 mM), 2-mercaptoethanol (50 μM), penicillin (50 units/ml) and streptomycin (50 μg/ml).

Regarding the cells, the human monocyte strain THP-1 cells cultivated in the foregoing culture medium were centrifuged at 100 xg for 5 minutes to remove the supernatant and then again suspended in a fresh culture medium prior to the practical use. The LPS used herein was derived from S. Typhimurium and this was dissolved in purified water and then this was dissolved in purified water and then diluted with the culture medium prior to use. Each compound to be tested was dissolved in dimethyl sulfoxide (DMSO) and diluted with the culture medium prior to the practical use.

The cells ($10^6$ cells/ml) prepared according to the foregoing method were admixed with the LPS (2 μg/ml) and a compound to be tested ($10^{-5}$M), the cells were incubated at 37° C. for two hours and then centrifuged at 1000 xg for 5 minutes. The resulting supernatant of the culture medium was inspected for the level of TNF-α using the human TNF-α -specific ELISA kit. In this connection, it was confirmed that the supernatant obtained by cultivating the cells in the culture medium free of any LPS (control) never included any TNF-α.

The rate of the TNF-α production inhibitory effect observed for each candidate compound was determined according to the following equation:

$$\text{Rate of Inhibition } (\%) = 100 \times (A-B)/A$$

Wherein A is the level of TNF-α detected in the supernatant obtained from the culture medium free of any candidate compound and B is the level of TNF-α detected in the supernatant obtained from the culture medium containing a candidate compound.

(Results)

A few test results, by way of example, or the inhibitory rate (%) of TNF-α. production observed at the concentration of $10^{-5}$M are shown in the following Table 1.

TABLE 1

| Candidate Compound | Inhibitory Rate (%) |
|---|---|
| Compound 3-6 | 94 |
| Compound 3-13 | 66 |
| Compound 6-2 | 58 |

As will be seen from the results listed in Table 1, it was recognized that the compounds of the present invention show the TNF-α production inhibitory effect at a low concentration.

2) In Vivo Test

Animals used herein were about 7-week-old female mice (5 animals per group) having a body weight of about 20 g. The LPS herein used was derived from Salmonella and it was dissolved in phosphate-buffered physiological saline prior to the practical use (20 μg/ml). Each candidate compound was dissolved or suspended in a 2% dimethyl sulfoxide-containing physiological saline to give a uniform solution or suspension (1 mg/ml).

The LPS solution (10 ml/kg) prepared above was intraperitoneally administered to each test mouse. Immediately after the administration of the LPS solution, the solution of each candidate compound prepared above (10 ml/kg, containing 10 mg/kg of the candidate compound) was subcutaneously injected to each animal. After one hour from the administration of the LPS, each animal was decapitated, the blood was collected from the animal and the blood was centrifuged at 4° C., 3000 rpm for 5 minutes. The resulting plasma was inspected for the level of TNF-α using the mouse TNF-α -specific ELISA kit. In this connection, any TNF-α was not detected in the plasma derived from the animal group free of the LPS-administration (control group).

The rate of TNF-α production-inhibitory effect observed for each candidate compound was determined according to the following equation:

Inhibitory Rate (%)=100×(A−B)/A

Wherein A is the level of TNF-α detected in the plasma derived from the animal group to which any candidate compound was not administered and B is the level of TNF-α detected in the plasma derived from the animal group to which a candidate compound was administered.

(Results)

The inhibitory rates (%) of TNF-α production observed when each candidate compound was subcutaneously administered at a dose of 10 mg/kg are shown in the following Table 2.

TABLE 2

| Candidate Compound | Inhibitory Rate (%) |
|---|---|
| Compound 3-2 | 50 |
| Compound 3-3 | 64 |
| Compound 3-4 | 51 |
| Compound 3-9 | 76 |
| Compound 3-17 | 52 |
| Compound 6-1 | 78 |
| Compound 6-3 | 50 |
| Compound 6-4 | 59 |

As has been discussed above in detail, the compound of the present invention has an excellent TNF-α production inhibitory effect and it is clear that the compound has wide variety of applications as pharmaceutical agents such as therapeutic agents for diseases, in which TNF-α is involved, for instance, autoimmune diseases such as chronic articular rheumatism, Crohn's disease and systemic erythematodes, dyscrasia, acute infectious diseases, allergy, fever, anemia and diabetes.

What is claimed is:

1. An N-substituted-N'-substituted urea derivative represented by the following general formula I or a pharmaceutically acceptable salt thereof:

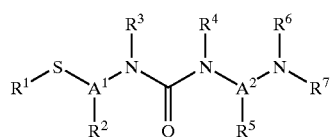

(I)

wherein $R^1$ represents a hydrogen atom, a lower alkyl group, an aryl group or a group represented by the following general formula II:

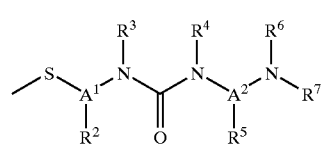

(II)

wherein $R^2$ represents a hydrogen atom, a lower alkyl group, a cycloalkyl group, an aryl group, a carboxyl group or an ester group, or $R^2$ may form a ring together with $R^1$; $R^3$ and $R^4$ may be the same or different and each represents a hydrogen atom, a lower alkyl group, a cycloalkylalkyl group, an adamantylalkyl group, an arylalkyl group, a cycloalkyl group or an aryl group; $R^5$ represents a hydrogen atom, a lower alkyl group, a hydroxyl group, a lower alkoxy group or an aryl group; $R^6$ and $R^7$ may be the same or different and each represents a hydrogen atom, a lower alkyl group, a cycloalkylalkyl group, a cycloalkyl group or an aryl group; $A^1$ and $A^2$ may be the same or different and each represents a lower alkylene group, provided that $R^5$ and either $R^6$ or $R^7$ together or $R^6$ and $R^7$ together form a 5- to 7-membered ring, wherein said 5- to 7-membered ring is not an aromatic heterocyclic ring, and that either of $R^3$ and $R^4$ represents a cycloalkylalkyl group, an adamantylalkyl group or an arylalkyl group.

2. The urea derivative or a pharmaceutically acceptable salt thereof as set forth in claim 1, wherein $R^1$ is a hydrogen atom or a lower alkyl group, $R^2$ is a hydrogen atom or an aryl group, $R^3$ and $R^4$ may be the same or different and each represents a hydrogen atom, a lower alkyl group, a cycloalkylalkyl group, an adamantylalkyl group or an arylalkyl group, $R^5$ is a hydrogen atom, a lower alkyl group, a hydroxyl group or an aryl group, $R^6$ and $R^7$ may be the same or different and each represents a hydrogen atom, a lower alkyl group or an aryl group, and $A^1$ and $A^2$ may be the same or different and each represents an alkylene group having 2 and 3 carbon atoms.

3. The urea derivative or a pharmaceutically acceptable salt thereof as set forth in claim 2, wherein $R^6$ and $R^7$ represent hydrogen atoms or lower alkyl groups, $A^1$ is an alkylene group having 2 carbon atoms and $A^2$ is an alkylene group having 2 or carbon atoms.

4. The urea derivative or a pharmaceutically acceptable salt thereof as set forth in claim 1, wherein $R^3$ is a cycloalkylalkyl group, an adamantylalkyl group or an arylalkyl group and $R^4$ is a hydrogen atom.

5. The urea derivative or a pharmaceutically acceptable salt thereof as set forth in claim 1, wherein $R^5$ is a hydrogen atom, a lower alkyl group or an aryl group, $R^6$ and $R^7$ form a 5- to 7-membered ring together.

6. The urea derivative or a pharmaceutically acceptable salt thereof as set forth in claim 5, wherein the 5- to 7-membered ring formed from $R^6$ and $R^7$ optionally consists of a nitrogen, oxygen or sulfur atom, or a double bond.

7. The urea derivative or a pharmaceutically acceptable salt thereof as set forth in claim 1, wherein $R^5$ and $R^6$ or $R^7$ form a 5- to 7-membered ring and $R^6$ or $R^7$, which is not involved in the formation of a ring, is a lower alkyl group.

8. An N-substituted-N'-substituted urea derivative represented by the following general formula I or a pharmaceutically acceptable salt thereof:

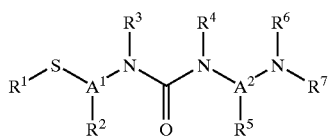

(I)

wherein $R^1$ is a hydrogen atom protected with a lower alkylcarbonyl group; $R^2$ represents a hydrogen atom, a lower alkyl group, a cycloalkyl group, an aryl group, a carboxyl group or an ester group, or $R^2$ may form a ring together with $R^1$; $R^3$ and $R^4$ may be the same or different and each represents a hydrogen atom, a lower alkyl group, a cycloalkylalkyl group, an adamantylalkyl group, an arylalkyl group, a cycloalkyl group or an aryl group; $R^5$ represents a hydrogen atom, a lower alkyl group, a hydroxyl group, a lower alkoxy group or an aryl group; $R^6$ and $R^7$ may be the same or different and each represents a hydrogen atom, a lower alkyl group, a cycloalkylalkyl group, a cycloalkyl group or an aryl group; $A^1$ and $A^2$ may be the same or different and each represents a lower alkylene group, provided that $R^5$ and either $R^6$ or $R^7$ together or $R^6$ and $R^7$ together form a 5- to 7-membered ring, wherein said 5- to 7-membered ring is not an aromatic heterocyclic ring, and that either of $R^3$ and $R^4$ represents a cycloalkylalkyl group, an adamantylalkyl group or an arylalkyl group.

9. A compound selected from the group consisting of 1-(2-(acetylthio)-ethyl)-1-(2-cyclohexylethyl)-3-(2-(1-pyrrolidinyl) ethyl) urea, 1-(2-(acetylthio)-ethyl)-1-(2-cyclohexylethyl)-3-(3-(1-pyrrolidinyl) propyl) urea, 1-(2-(acetylthio) ethyl)-1-(2-cyclohexylethyl)-3-(3-(1-piperidyl) propyl) urea, 1-(2-(acetylthio) ethyl)3-3((1S)-1-benzyl-2-(4-methnylpiperazin-1-yl) ethyl)-1-phenethyl urea, 1-(2-(acetylthio) ethyl)-1-(2-cyclohexylethyl)-3-(2-(1-homopiperidyl) ethyl) urea, 1-(2-(acetylthio) ethyl)-1-(2-cyclohexylethyl)-3-(2-(1,2,5,6-tetrahydropyridin-1-yl) ethyl) urea, 1-(2-(acetylthio) ethyl)-1-(2-cyclohexylethyl)-3-(((2RS)-1-ethyl-2-pyrrolidinyl) methyl) urea, 1-(2-(acetylthio) ethyl)-1-(2-cyclohexylethyl)-3-(2-(1-piperidyl) ethyl) urea, 1-(2-(acetylthio) ethyl)-1-(2-cyclohexylethyl)-3-(2-(4-(dimethylamino)-1-piperidyl)-ethyl) urea, 1-(2-(acetylthio) ethyl)-1-(2-cyclohexylethyl)-3-((1-methyl-4-piperidyl) methyl) urea and 1-(2-cyclohexylethyl)-1-(2-(methylthio)ethyl)-3-(2-(1-piperidyl) ethyl) urea or pharmaceutically acceptable salts thereof.

10. An N-substituted-N'-substituted urea derivative represented by the following general formula III or a salt thereof:

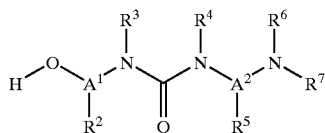

(III)

wherein $R^2$ represents a hydrogen atom, a lower alkyl group, a cycloalkyl group, an aryl group, a carboxyl group or an ester group, or $R^2$ may form a ring together with $R^1$; $R^3$ and $R^4$ may be the same or different and each represents a hydrogen atom, a lower alkyl group, a cycloalkylalkyl group, an adamantylalkyl group, an arylalkyl group, a cycloalkyl group or an aryl group; $R^5$ represents a hydrogen atom, a lower alkyl group, a hydroxyl group, a lower alkoxy group or an aryl group; $R^6$ and $R^7$ may be the same or different and each represents a hydrogen atom, a lower alkyl group, a cycloalkylalkyl group, a cycloalkyl group or an aryl group; $A^1$ and $A^2$ may be the same or different and each represents a lower alkylene group, provided that $R^5$ and either $R^6$ or $R^7$ together or $R^6$ and $R^7$ together form a 5- to 7-membered ring, and that either of $R^3$ and $R^4$ represents a cycloalkylalkyl group, an adamantylalkyl group or an arylalkyl group.

11. A pharmaceutical composition containing an N-substituted-N'-substituted urea derivative or a pharmaceutically acceptable salt thereof as set forth in claim 1.

12. A pharmaceutical composition comprising an N-substituted-N'-substituted urea derivative or a pharmaceutically acceptable salt thereof as set forth in claim 2.

13. A pharmaceutical composition comprising an N-substituted-N'-substituted urea derivative or a pharmaceutically acceptable salt thereof as set forth in claim 9.

14. A method of inhibiting TNF-α production comprising administering to a patient in need of such inhibition an N-substituted-N'-substituted urea derivative or a pharmaceutically acceptable salt thereof as set forth in claim 1.

15. A method of inhibiting TNF-α production which comprises administering to a patient in need of such inhibition the N-substituted-N'-substituted urea derivative or a pharmaceutically acceptable salt thereof as set forth in claim 2.

16. A method for inhibiting TNF-α production in a patient in need of such inhibition comprising administering to said patient the N-substituted-N'-substituted urea derivative or a pharmaceutically acceptable salt thereof as set forth in claim 9.

17. A method for treating autoimmune diseases comprising administering to a patient in need of such treatment an N-substituted-N'-substituted urea derivative or a pharmaceutically acceptable salt thereof as set forth in claim 1.

18. A method for treating autoimmune diseases comprising administering to a patient in need of such treatment the N-substituted-N'-substituted urea derivative or a pharmaceutically acceptable salt thereof set forth in claim 2.

19. A method for treating autoimmune diseases comprising administering to a patient in need of such treatment the N-substituted-N'-substituted urea derivative or a pharmaceutically acceptable salt thereof as set forth in claim 9.

* * * * *

UNITED STATES PATENT AND TRADEMARK OFFICE
CERTIFICATE OF CORRECTION

PATENT NO.    : 6,534,499 B2
DATED         : March 18, 2003
INVENTOR(S)   : Shiro Mita et al.

It is certified that error appears in the above-identified patent and that said Letters Patent is hereby corrected as shown below:

Column 15,
After line 7 and before the formula please insert the following information:
--

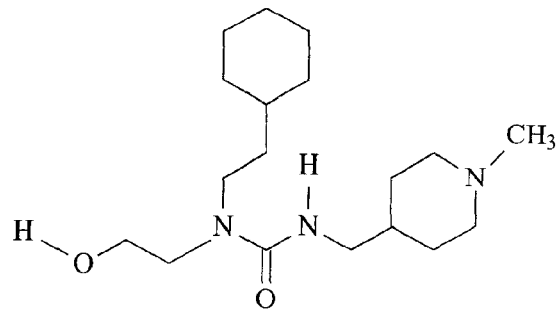

Lithium aluminum hydride (117 mg) was suspended in anhydrous ether (10 ml) with ice cooling in the nitrogen gas atmosphere, followed by the dropwise addition of a solution of 3-(2-cyclohexylethyl)-3-(2-hydroxyethyl)-1-[[1-(benzyloxycarbonyl)-4-piperidyl]methyl] urea (Compound 1-18, 454 mg) in anhydrous tetrahydrofuran (5 ml) to the resulting suspension. The mixture was stirred at room temperature for 45 minutes. To the reaction liquid, there were gradually and dropwise added ethyl acetate and 1N hydrochloric acid till the reaction liquid did not undergo foaming any more and 1N hydrochloric acid was further added to the reaction liquid. Then ether was added thereto to wash the liquid. To the resulting aqueous phase, there was added a 2N aqueous solution of sodium hydroxide to make the reaction liquid basic and then the aqueous phase was extracted with chloroform. The resulting organic phase was dried over anhydrous sodium sulfate and then concentrated under reduced pressure to give the title compound
(Compound 2-1, 361 mg).
(Compound 2-1)

UNITED STATES PATENT AND TRADEMARK OFFICE
CERTIFICATE OF CORRECTION

PATENT NO. : 6,534,499 B2
DATED : March 18, 2003
INVENTOR(S) : Shiro Mita et al.

It is certified that error appears in the above-identified patent and that said Letters Patent is hereby corrected as shown below:

Column 15 (cont'd),
  IR (Film, $cm^{-1}$): 3328, 2922, 2850, 2784, 1629, 1540, 1448, 1406, 1374, 1276 and 1154
Example 3: 1 -[2-Acetylthio) ethyl]-1-(2-cyclohexylethyl)-3-[2-(1-piperidyl)ethyl] urea (Compound 3-1) --

Signed and Sealed this

Seventh Day of October, 2003

JAMES E. ROGAN
*Director of the United States Patent and Trademark Office*